(12) United States Patent
Attariwala

(10) Patent No.: US 11,158,029 B2
(45) Date of Patent: Oct. 26, 2021

(54) DISTORTION CORRECTION OF MULTIPLE MRI IMAGES BASED ON A FULL BODY REFERENCE IMAGE

(71) Applicant: VIGILANCE HEALTH IMAGING NETWORK INC., Montréal (CA)

(72) Inventor: Rajpaul Attariwala, Vancouver (CA)

(73) Assignee: VIGILANCE HEALTH IMAGING NETWORK INC., Montréal (CA)

( * ) Notice: Subject to any disclaimer, the term of this patent is extended or adjusted under 35 U.S.C. 154(b) by 0 days.

(21) Appl. No.: 16/076,675

(22) PCT Filed: Feb. 12, 2016

(86) PCT No.: PCT/CA2016/050132
§ 371 (c)(1),
(2) Date: Aug. 8, 2018

(87) PCT Pub. No.: WO2017/136914
PCT Pub. Date: Aug. 17, 2017

(65) Prior Publication Data
US 2019/0050965 A1    Feb. 14, 2019

(51) Int. Cl.
*G06T 5/00* (2006.01)
*G01R 33/565* (2006.01)
(Continued)

(52) U.S. Cl.
CPC .............. *G06T 5/001* (2013.01); *A61B 5/055* (2013.01); *G01R 33/3875* (2013.01);
(Continued)

(58) Field of Classification Search
CPC ........ A61B 5/7289; A61B 2017/00694; A61B 6/12; A61B 6/504; A61B 8/0891;
(Continued)

(56) References Cited

U.S. PATENT DOCUMENTS 5,614,827 A    3/1997 Heid
2002/0167319 A1*  11/2002 Ikezaki ............ G01R 33/56554
                                                     324/307
(Continued)

FOREIGN PATENT DOCUMENTS

JP           8275929       10/1996
JP      2008086748 A        4/2008
(Continued)

OTHER PUBLICATIONS

International Search Report and Written Opinion received for PCT Appl. No. PCT/CA2016/050132 dated Oct. 17, 2016.
(Continued)

*Primary Examiner* — Ajibola A Akinyemi
(74) *Attorney, Agent, or Firm* — Dorsey & Whitney LLP

(57) ABSTRACT

Methods, systems, products, devices, and/or apparatus generally related to distortion correction of multiple MRI images based on a full body reference image. An example method for distortion correction of multiple MRI images based on a full body reference image may include acquiring at least one reference image of a subject using a magnetic resonance imaging system, storing a correction field map based on the at least one reference image, the correction field map including information regarding a correction field for each of a plurality of portions of the subject, acquiring a plurality of images by the magnetic resonance imaging system, each of the plurality of images corresponding to a respective portion of the subject, and while acquiring each of the plurality of images, applying a correction field specified by the correction field map for the respective portion of the subject.

23 Claims, 4 Drawing Sheets

(51) Int. Cl.
*A61B 5/055* (2006.01)
*G01R 33/3875* (2006.01)
*G01R 33/561* (2006.01)
*G06T 5/50* (2006.01)
*G01R 33/24* (2006.01)

(52) U.S. Cl.
CPC ....... *G01R 33/565* (2013.01); *G01R 33/5615* (2013.01); *G01R 33/56563* (2013.01); *G06T 5/50* (2013.01); *G01R 33/243* (2013.01); *G06T 2207/10088* (2013.01)

(58) Field of Classification Search
CPC ...... A61B 18/1492; A61B 2017/00252; A61B 2017/00703; A61B 2017/22044; A61B 2017/22094; A61B 6/503; A61B 6/5217; A61B 6/541; A61B 8/0883; A61B 8/543; A61B 5/0044; A61B 6/5247; A61B 2090/365; A61B 34/20
USPC ......................................................... 382/275
See application file for complete search history.

(56) References Cited

U.S. PATENT DOCUMENTS

| | | | |
|---|---|---|---|
| 2009/0256567 A1* | 10/2009 | Aksit | G01R 33/56563 324/312 |
| 2010/0016724 A1* | 1/2010 | Arai | A61B 8/08 600/443 |
| 2010/0244823 A1 | 9/2010 | Abe et al. | |
| 2011/0103668 A1* | 5/2011 | Uchizono | G01R 33/561 382/131 |
| 2012/0032676 A1 | 2/2012 | Dannels | |
| 2012/0319686 A1* | 12/2012 | Jesmanowicz | G01R 33/446 324/309 |
| 2014/0239949 A1* | 8/2014 | Huang | G01R 33/543 324/307 |
| 2014/0361770 A1 | 12/2014 | Dannels | |
| 2015/0168517 A1 | 6/2015 | Shen et al. | |
| 2015/0241537 A1 | 8/2015 | Dannels | |
| 2016/0131732 A1* | 5/2016 | Pfeuffer | G01R 33/56563 324/322 |

FOREIGN PATENT DOCUMENTS

| | | |
|---|---|---|
| WO | 2007113992 A1 | 10/2007 |
| WO | 2008086748 A1 | 7/2008 |
| WO | 2011155461 A1 | 12/2011 |
| WO | 2017136914 A1 | 8/2017 |

OTHER PUBLICATIONS

Cusack, et al., "An Evaluation of the Use of Magnetic Field Maps to Undistort Echo-Planar Images", NeuroImage 18, 127-142 (2003), dol:10.1006/nimg.2002.1281, httn://www.cusacklab.org/:gdfs/cusack_et_al-fieldman_undistort_ni2003.pd (Apr. 2002).

Jezzard, "Shim Coil Design, Limitations and Implications", FMRIB Centre, John Radcliffe Hospital, Headington, Oxford OX3 9DU, England; accessed at http://mri-q.com/uploads/3/2/7/4/3274160/shim_coil_design_jezzard.pdf on Jan. 11, 2016.

Extended European Search Report dated Sep. 6, 2019 for European Application No. 16889683.5, 8 pages.

English Translation of First Office Action for Japanese Application No. 2018-542177 dated Aug. 5, 2019.

Sengupta, et al., "Whole-Body Continuously Moving Table Fat-Water MRI with Dynamic B0 Shimming at 3 Tesla," Magnetic Resonance in Medicine, 2015, at 76:183-190.

English translation of Decision to Grant a Patent for JP Application No. 2018-542177, dated Feb. 8, 2021.

English translation of Notification of Reasons for Refusal for JP Application No. 2018-542177, dated Jul. 8, 2020.

Office Action for CA Application No. 3,013,939, dated Jun. 10, 2020.

* cited by examiner

DISTORTION CORRECTION OF MULTIPLE MRI IMAGES BASED ON A FULL BODY REFERENCE IMAGE

CROSS-REFERENCE TO RELATED APPLICATIONS

This application is a U.S. National Stage filing under 35 U.S.C. § 371 of PCT Application No. PCT/CA2016/050132, filed Feb. 12, 2016, which is incorporated herein by reference, in its entirety, for any purpose.

BACKGROUND

Magnetic imaging continues to gain acceptance for patient analysis. The images allow a physician to image the internal structure of a patient and make treatment recommendations. The use of magnetic imaging, however, is typically performed after the problem area has been isolated, or at least determined based on some pre-diagnosis. While magnetic imaging is useful in targeted situations, whole body magnetic imaging has yet to gain widespread adoption, in part due to various issues that arise when acquiring whole body images. For example, distortion, which may be due in part to the capabilities of the imagers and the imaging sequence itself, plague magnetic imaging techniques.

SUMMARY

Techniques are generally described that include methods and systems. An example method may include acquiring at least one reference image of a subject using a magnetic resonance imaging system, storing a correction field map based on the at least one reference image, the correction field map including information regarding a correction field for each of a plurality of portions of the subject, acquiring a plurality of images by the magnetic resonance imaging system, each of the plurality of images corresponding to a respective portion of the subject, and while acquiring each of the plurality of images, applying a correction field specified by the correction field map for the respective portion of the subject.

An example computer program includes at least one non-transitory computer-readable medium encoded with executable instructions, that when executed by a computing system, causes the computing system to acquire one or more reference images of a subject using a magnetic resonance imaging machine, store a correction field map based on the one or more reference images, the correction field map including information regarding correction fields for portions of the subject, acquire a plurality of images of portions of the subject using the magnetic resonance imaging system, while acquiring each of the plurality of images of portions of the subject, apply correction fields specified by the correction field map for the portions of the subject, wherein the correction fields are provided by one or more correction coils of the magnetic resonance imaging system, and generate a composite image based on the plurality of images.

An example system includes a magnetic resonant imaging system including a main coil and a plurality of correction coils, wherein the main coil and the correction coils provide respective magnetic fields responsive to receiving respective control signals, and a computing system coupled to the magnetic resonance imaging system. The computing system may be configured to provide control signals to the magnetic resonance imaging system to cause the magnetic resonance imaging system to acquire one or more reference images of a patient's body using a magnetic field provided by the main coil, apply correction magnetic fields through at least one of the plurality of correction coils while acquiring each of a plurality of sub-images of the patient, wherein the correction field applied during the acquisition of each of the plurality of sub-images is determined based on a respective portion of the one or more reference images, and wherein the main coil provides a main magnetic field while acquiring each of the plurality of sub-images, and provide a composite image of the patient based on the plurality of sub-images.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which:

Figure 1:
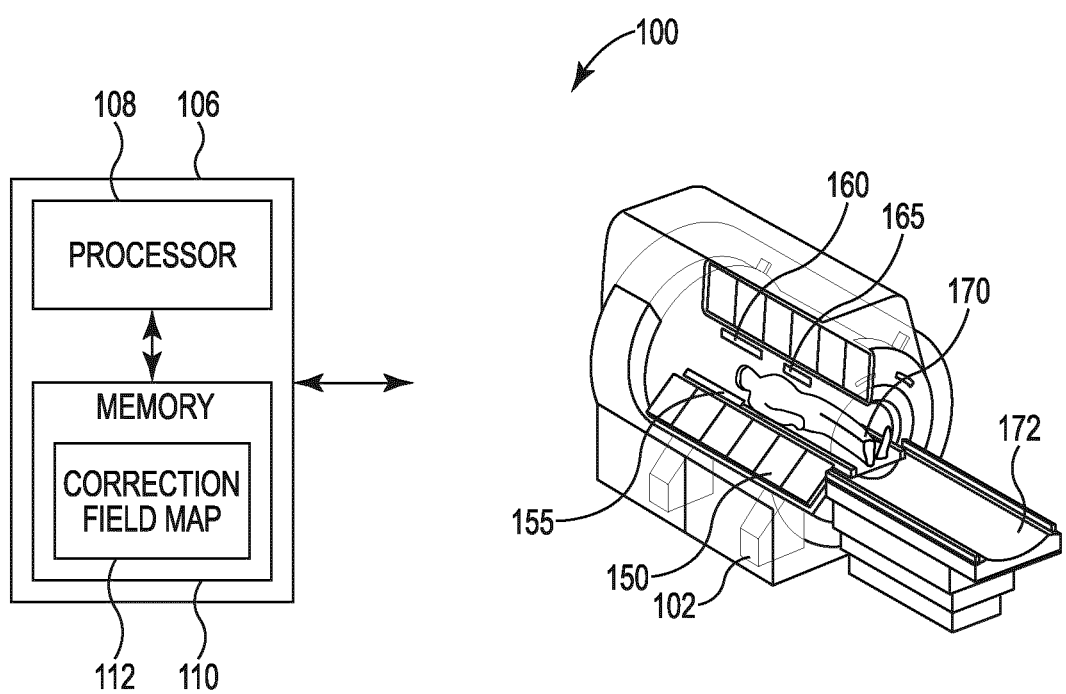
FIG. 1 is a schematic illustration of a system arranged in accordance with at least some embodiments described herein.

all arranged in accordance with at least some embodiments of the present disclosure.

DETAILED DESCRIPTION

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are implicitly contemplated herein.

This disclosure is drawn, inter alia, to methods, systems, products, devices, and/or apparatus generally related to distortion correction of multiple MRI images based on a full body reference image. An example method for distortion correction of multiple MRI images based on a full body reference image may include acquiring at least one reference image of a subject using a magnetic resonance imaging system, storing a correction field map based on the at least one reference image, the correction field map including information regarding a correction field for each of a plurality of portions of the subject, acquiring a plurality of images by the magnetic resonance imaging system, each of the plurality of images corresponding to a respective portion of the subject, and while acquiring each of the plurality of images, applying a correction field specified by the correction field map for the respective portion of the subject.

Throughout the following descriptions and example, the illustrative descriptions of the invention are described in the context of generating spatially accurate whole body MR images for diagnosis and/or treatment. However, it is to be understood that examples of the present invention may be applied to generating spatially accurate composite images from virtually any imaging device that requires stitching of multiple partial member images.

FIG. 1 is a schematic illustration of a system 100 arranged in accordance with at least some embodiments described herein. FIG. 1 shows a magnetic resonance imaging system 102 coupled to a computing system 106. The magnetic resonance imaging system 102 may have a table 172 for placing a patient 170. The patient may be then transported into a bore of the magnetic resonance imaging system 102. The magnetic resonance imaging system may include main coil 150, one or more gradient coils, such as the coil 155, one or more RF coils, such as the coil 160, and one or more correction coils, such as the coil 165. The computing system 106 may at least include a processor 108, and a memory 110, which may include a correction field map 112. The various components described in FIG. 1 are merely examples, and other variations, including eliminating components, combining components, and substituting components are all contemplated.

The magnetic resonance imaging (MRI) system 102 may provide one or more magnetic fields to a patient located within a bore of the MRI system 102. The MRI system 102 may generally include a bore configured to receive a subject and coils to provide a magnetic field within the bore to generate one or more MRI images. The MRI system 102 may include a main coil 150 to generate a magnetic field sufficient to generate an MRI image. The MRI system 102 may also include RF coils, such as the coil 160, to provide an RF field to all or a portion of the bore. In some examples, the RF coils may be integrated into a same instrument housing the coils used to provide a magnetic field and/or may be integral with other coils used to provide a magnetic field. In some examples, the RF coils may be provided in a separate device positioned to provide RF energy to the bore. Only a portion of the RF coil 160 is shown in FIG. 1 in cross-section—other geometries, cross-sections, and positions are possible in other examples. The MRI system 102 may include one or more gradient coils, such as the coil 155, positioned to provide gradient magnetic fields through the bore. Only a portion of the gradient coil 155 is shown in FIG. 1 in cross-section—other geometries, cross-sections, and positions are possible in other examples.

The MRI system 102 may include one or more correction coils, such as the coil 165. The correction coils may provide a magnetic field in the bore which may compensate for irregularities in the magnetic field which may be caused, for example, by the patient themselves. Only a portion of the correction coil 165 is shown in FIG. 1 in cross-section—other geometries, cross-sections, and positions are possible in other examples. Moreover, in some examples, one or more of the correction coils, including the correction coil 165 may be integrated with one or more of the other coils described herein.

Generally any subjects may be imaged in accordance with techniques described herein including, but not limited to humans (including adults and children) and animals (including cattle, horses, dogs, and cats).

Main magnet field strengths used in the imaging described herein may generally range from 0.5 to 3 Tesla, although other field strengths may also be used.

Generally, when a subject is placed in the bore of the MRI system and a magnetic field provided in the bore, the magnetic moments of protons within the subject may be aligned along the direction of the magnetic field. When imaging a subject, RF pulses may be delivered by the RF coils of the magnetic resonance imaging system. The RF pulses may have the effect of tilting the magnetic moments of the protons away from their equilibrium direction. The magnetic moments then return to equilibrium while precessing about the magnetic field, which in turn induces an RF response signal in the RF coils. Generally, a human body may be considered to include significant amounts of water molecules, which each water molecule containing 2 protons that generally dominate the RF response signal. The RF response signal induced in the coils may be related to the time that it takes the protons to return to equilibrium following excitation, e.g., a relaxation time. The relaxation time may in turn depend on the local environment, e.g., tissue structure, tissue density, etc., within the patient, leading to visible changes in image contrast throughout the subject.

The received RF response signal may not on its own provide any spatial information because it may have contributions from every position within the subject. Spatial frequency components (e.g. kx, ky, kz) of the RF response may be measured and related to spatial positions through a Fourier Transform to generate a 3D image of the subject.

In some examples, the MRI system 102 may provide additional gradient magnetic fields that vary linearly in a given spatial direction. Gradient magnetic fields may in some examples be applied during RF pulse application rather than during read-out. RF pulses may be designed to selectively excite the frequencies that correspond to the resonant frequencies of the protons in the subject within a small range of gradient values. This selective excitation may provide a signal that originates from a 2D slice of finite thickness through the subject, for example an axial, sagittal or coronal slice. A 2D inverse Fourier Transform may be used to generate the pixel values of the slice. Successive slices can be acquired at various locations and amalgamated to provide a slice-by-slice 3D representation of the patient.

It may be desirable in some examples to have the provided magnetic field and any gradient magnetic field be as homogeneous as possible. Inhomogeneities may cause spatial distortions in MRI images that may depend upon the RF pulse sequence used. Some inhomogeneities may be subject-specific. The subject-specific inhomogeneities may vary from subject to subject due to each patient having unique spatial distributions of magnetic field susceptibility based on their anatomy. The variation from subject to subject may create a unique pattern of magnetic field spatial distortion for each subject. Subject-specific magnetic field distortions may be generally be corrected through a technique called shimming, which may use additional coils (e.g. correction coils, such as the correction coil 165) to generate a correction magnetic field, e.g., a shimming field, that may be provided to correct in some examples for inhomogeneities in the main magnetic field which may, for example, be due to the patient's anatomy.

Accordingly, the magnetic resonance imaging system 102 may include at least a first magnetic coil, e.g. a main magnetic coil 150, configured to provide a magnetic field in the bore sufficient to generate an MRI image. The main magnetic coil, for example, may be provided such that it surrounds the patient throughout a substantial length of the bore. Moreover, RF coils and/or gradient coils, such as the coils 155 and 160 of FIG. 1 may be used to generate a magnetic field for MRI imaging. The magnetic resonance imaging system 102 may further include one or more additional coils (e.g. correction coils), such as the coil 165, which may provide additional magnetic fields in the bore which may be reduce or eliminate inhomogeneity in the magnetic field provided by the main coil, the RF coil(s), and/or the gradient coil(s) in the presence of a subject. The magnetic field generated by the correction coils in combination with the main and/or other coils may produce a homogeneous magnetic field (or a magnetic field having improved homogeneity) in the presence of the subject when added to the main magnetic field, e.g., a combined magnetic field.

The correction coils may include one or a plurality of individual coils that may be controlled individually in order to provide magnetic fields of different strengths, different spherical harmonics, and/or at different frequencies. In some embodiments, some of the correction coils may be superconducting, e.g. 5-20 coils located within the MRI cryostat, and/or be resistive, e.g. mounted with the gradient coils at room temperature. In some embodiments, the gradient coils themselves may be used as correction coils through application of a small bias offset current. In some embodiments, at least 5 additional resistive coils are used, including a series of individual wire windings or etchings on cylindrical copper sheets. In some embodiments, the correction coils may be implemented using a combination of ring-shaped axial coils and/or saddle-shaped transverse coils. In some embodiments, the correction coils may include matrix coils that may in some examples improve accuracy of corrections and efficiency. In some embodiments, main coils for generating a main magnetic field, gradient coils for generating directional gradient fields, and correction coils for generating the correction fields may be integral with the MRI system 102. In some embodiments, RF coils may also be positioned within the bore, or in some cases within a moveable apparatus that may be positioned in close proximity to the subject, which may be used to obtain a higher signal to noise ratio in some examples. The main magnetic coil(s) and the correction coils may be independently controlled to provide respective magnetic fields into the bore of the MRI system 102 in some examples. In some embodiments, the magnetic field provided by the correction coils may interact with the magnetic field provided by the main coils to reduce or eliminate inhomogeneities of the magnetic field of the main coils due to the presence of a patient.

For example, the combined field generated by the combination of main magnetic field and at least one correction magnetic field may be more uniform than the main magnetic field alone, particularly when a subject is present in the bore.

The computing system 106 may include one or more processing units (e.g. processor 108) and memory 110. The memory may be encoded with executable instructions for performing the functions described herein, e.g. storing a correction field map based on one or more reference images and providing correction field information to the MRI system 102 or operating the MRI system 102 with the correction fields specified by the correction field map. The memory may be in some examples encoded with the correction field map 112 itself. Computing system 106 may provide one or more control signals to the MRI system 102. The control signals may be provided using a wired or wireless connection. The computing system 106 may provide control signals to the MRI system 102 to apply certain correction fields during imaging of a subject. The correction fields may be determined based on reference to a correction field map which may be stored in the memory 110. The correction field map may be based on a reference image of the subject (e.g. a full-body image). By obtaining a reference image of the subject and utilizing the reference image to provide a correction field map for later imaging of portions of the subject, the subsequent imaging may be made more efficient in some examples. For example, the correction field map may provide correction fields to be used for each position along a length of a patient, and those correction fields may be used during a subsequent full-body imaging of the patient. In some examples, the correction field map may provide correction fields to be used for certain portions along a length of a patient (e.g. certain body parts, organs, tissues). When imaging that portion of the patient, the appropriate correction field may be used. This may avoid a need in some examples to first take an image of a portion of the subject to be imaged, calculate a correction field, then utilize the correction field to image the portion of the subject before repeating the process for any other imaged portions. Instead, a single correction field map may be generated from a reference image (e.g. a whole-body reference image) and the single correction field map may be accessed to provide correction fields for subsequent imaging of all or portions of the subject. It is to be understood that the computing system 106 used to provide control signals for the correction fields to the MRI system 102 may or may not be a same computing system used to operate the MRI system 102 to obtain MRI images.

Utilizing a single reference image, as opposed to one reference image per body section imaged, may provide advantages in some examples. In some examples, such an approach may save approximately 10-15 percent of the total scan time. For example, instead of lasting 60 minutes for a whole body scan, which may include about 12 sequences, the whole body scan may last 50 minutes. For a spine scan, which may include about 3-4 sequences, the scan may take 25 minutes instead of 30 minutes in some examples.

During operation, the computing system 106 (and/or another computing system) may control the MRI system 102 to obtain one or more reference images of a subject located in the bore of the MRI system 102. In some examples, the subject may be translated through the bore, continuously or step-wise, as reference images are obtained.

The one or more reference images may be low resolution images, which may subsequently be used by the computing system 106 to provide correction fields when taking higher resolution images. The reference images may be analyzed by the computing system 106 to identify inhomogeneity distributions in the reference images and calculate correction fields to reduce or eliminate inhomogeneity. The correction fields may be stored in a correction field map, where correction fields for each of a plurality of portions of the reference image may be stored. In some embodiments, the portion of the master reference image, and the correction field information, may be associated in accordance with a coordinate system of the MRI system 102. For example, the correction field map may map correction field information to coordinates of the MRI system 102. For example, the correction field map 112 may be specified in terms of spherical harmonics. The spherical harmonics may represent sums of basis functions, each basis function having a corresponding coefficient specifying a strength of that basis function in the correction field. The correction field map 112 may accordingly include coefficients for each basis function. A full distribution for the corresponding correction field may be restored by multiplying all the basis functions with their respective coefficients stored in the correction field map. When imaging certain coordinate of the MRI system 102, the associated correction field from the correction field map may be used. In some examples, the correction field map may map correction field information to features (e.g. body parts, regions, organs, tissues) of a subject. When imaging those features, the MRI system 102 may apply the appropriate correction field as reflected in the correction field map.

In some embodiments, the computing system 106 (and/or another computing system) may control the MRI system 102 to obtain a series of high resolution sub-images of the patient, which may be acquired using correction fields applied by correction coils based on a respective portion of a correction field map.

The processor 108 may be implemented, for example, using one or more central processing units (CPUs), with each CPU having one or more processing cores. The processor 108 may perform tasks using software (e.g. executable instructions) stored in the memory 110, for example. Additionally, the processor 108 may calculate correction fields and cause correction field maps to be stored.

The memory 110 may be generally any electronic storage, including volatile or nonvolatile memory, which may encode instructions for performing functions described herein. Additionally, the memory 110 may store images acquired by the MRI system 102 along with correction field maps. For example, the memory 110 may store one or more reference images, correction field maps, and one or more subsequent images taken with correction fields based on the correction field map 112.

The computing system 106 may provide correction field information to correction coils of the MRI system 102. For example, when the MRI system 102 acquires an image, MRI system 102 may receive correction field information from a correction field map based on a corresponding portion of the one or more reference images. Additionally, the computing system 106 may control a number of correction coils of the MRI system 102, which may be integral to or within the bore of the MRI system 102. In general, the correction coils may compensate for magnetic field inhomogeneities of the main magnetic field during subsequent image acquisition. The computing system may provide control signals to the correction coils that cause a current to flow through the correction coils to induce a desired correction magnetic field within the bore of the MRI system 102.

In an example operation, one or more reference images may be acquired by the MRI system 102 and stored in the memory 110. The one or more reference images may be of a full body of a patient. For example, imaging of a human patient my include acquiring one or more reference images of the patient's entire body, e.g., from head to toe. In some examples, only a portion of a body may be imaged for a reference image (e.g. toe to waist, waist to head).

The one or more reference images may be visually presented as coronal, sagittal, and axial slices or projection views from any direction. The one or more reference images may also be used, for example, to determine the field of view and placement of subsequent images taken using correction fields described herein.

Inhomogeneities may be analyzed in the reference images by various methods. For example, inhomogeneities may be mapped by collecting gradient echo images with different echo times, and then calculating the correction field from the phase difference between the master reference images. In some examples, "pencil" profiles of the gradient echo images may be collected along different directions to enable faster acquisitions.

In some embodiments, two reference images may be acquired, each with different gradient echo weightings. Two reference images acquired with different gradient echo weightings may allow the computing system 106 to determine a phase difference $\Delta\varphi$ between the two reference images. From the phase difference, the computing system may determine the magnetic field inhomogeneity through the equation $\Delta\varphi/(\gamma\Delta TE)$, where $\Delta\varphi$ is the phase difference between the two reference images, TE is the echo time, and $\gamma$ is the gyromagnetic ratio. In some examples, it may not be possible to accurately correct field distortions globally with low-order spherical harmonics. In such examples, field correction information may include slice-by-slice information, e.g., 2D, rather than over an entire 3D image.

The computing system may determine one or more inhomogeneity distributions based on the one or more reference images, and generate a correction field map including correction fields corresponding to portions of the reference image to reduce and/or eliminate the inhomogeneity. The one or more inhomogeneity distributions and/or correction field maps may be stored either as complete distributions or reduced dimensionality representations of the distributions. In some embodiments, the computing system 106 may analyze the harmonic content of the inhomogeneity distribution, using spherical harmonic analysis for example to determine correction field information and/or to generate the correction field map. The computing system 106 may identify unwanted harmonic components in the inhomogeneity distribution, and the correction fields may be calculated to reduce and/or eliminate the unwanted harmonic components. For example, the correction field information may include information to generate a compensating magnetic field for each unwanted harmonic component. In some embodiments, respective correction coils of a plurality of correction coils of the MRI system 102 may be used to compensate for each unwanted harmonic. The inhomogeneity information and/or correction field map may be stored in the memory 110 and/or in another storage accessible to the computing system 106.

In some embodiments, the inhomogeneity information and/or correction field map may be represented in terms of other parameters or functions to reduce the amount of data, or help smooth the distributions. In some embodiments, either the full data is maintained, or the data is represented as spherical harmonics. In others, the data may be represented as Fourier components, principal components, independent components, compressed data, or other data reduction techniques. Data can additionally be smoothed with, for example, low pass filters or convolution kernels, data fitting or other techniques known in the art.

Subsequent to the acquisition of the one or more reference images of the subject, a number of images may be acquired of the subject using correction fields corresponding to the correction fields stored in the correction field map. The plurality of images acquired using the correction fields may be acquired at a higher resolution than the one or more reference images. The plurality of images acquired using the correction fields may compositely also be of the patient's complete body in some examples. For example, the plurality of images may each represent a particular partial volume of the patient such as a torso, a head, legs, etc. During acquisition of the images, the computing system 106 may provide control signals to the correction coils of the MRI system 102 to produce a correction magnetic field that, when added to the main magnetic field, results in approximately a homogeneous magnetic field in the imaged portion. The computing system 106 may use correction field information stored in the memory 110 that corresponds to the portion of the patient of the sub-image. In some embodiments, the computing system 106 may utilize an optimization algorithm to find optimal adjustments of currents through each individual correction coil to ensure the magnetic field is as homogeneous as possible. In some embodiments, some regions that are not important to the optimization process may not be included in the optimization. In some embodiments, important regions may be weighted more heavily than less-important regions. The successive images may be stored in the memory 110 in some examples.

In this manner, multiple images may be obtained from a subject, with each image taken using a different correction field in accordance with a correction field map obtained from an earlier reference image. The reference image may include multiple regions of a subject. Subsequent images of the multiple regions may make use of different correction fields indicated by the correction field map. In this manner, it may not be necessary in some examples to take a reference image, calculate a correction field, and image the portion of the subject with the correction field, for each portion of a subject. Instead, one or more reference images are used to generate a correction field map applicable to multiple portions of a subject, and the MRI system may access the correction field map during acquisition of subsequent images to image multiple portions of a subject using different correction fields for different portions in accordance with the correction field map.

Following the acquisition of the images in the presence of correction fields, the computing system 106 may stitch the number of images together in some examples to generate a composite image of the patient, e.g., a whole body MRI image. The composite image may not suffer significantly from spatial distortions and thus may be relied upon for diagnosis and treatment in some examples.

Figure 2:
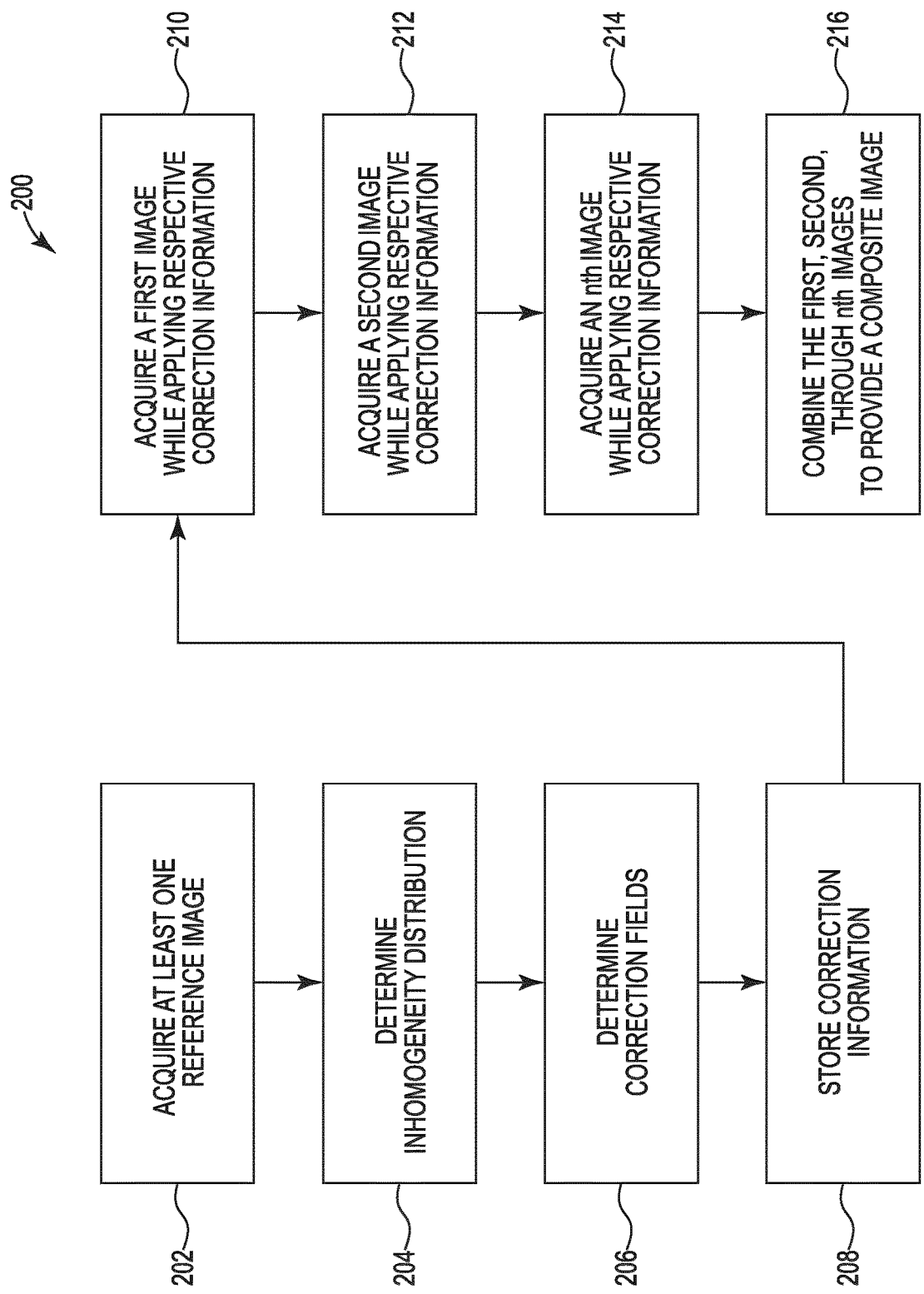
FIG. 2 is a an example method for imaging a subject arranged in accordance with at least some embodiments of the present disclosure

FIG. 2 is an example method 200 for imaging a subject arranged in accordance with at least some embodiments of the present disclosure. An example method may include one or more operations, functions or actions as illustrated by one or more of blocks 202, 204, 206, 208, 210, 212, 214, and/or 216. The operations described in the blocks 202 through 216 may be performed in response to execution (such as by one or more processors described herein) of computer-executable instructions stored in a computer-readable medium, such as a computer-readable medium of a computing device or some other controller similarly configured.

An example process may begin with block 202, which recites "acquire at least one reference image." Block 202 may be followed by block 204, which recites "determine inhomogeneity distribution." Block 204 may be followed by block 206, which recites "determine correction fields." Block 206 may be followed by block 208, which recites "store correction information." Block 208 may be followed by block 210, which recites "acquire a first image while applying respective correction fields." Block 210 may be followed by block 212, which recites, "acquire a second image while applying respective correction fields." Block 212 may be followed by block 214, which recites "acquire an nth image while applying respective correction fields." And block 214 may be followed by block 216, which recites "combine the first, second, through nth images to provide a composite image."

The blocks included in the described example methods are for illustration purposes. In some embodiments, the blocks may be performed in a different order. In some other embodiments, various blocks may be eliminated. In still other embodiments, various blocks may be divided into additional blocks, supplemented with other blocks, or combined together into fewer blocks. Other variations of these specific blocks are contemplated, including changes in the order of the blocks, changes in the content of the blocks being split or combined into other blocks, etc. In some examples, two reference images may be acquired using different gradient echo weightings and correction information may be determined from the two reference images based at least in part on a difference in angle of the two reference images due to the different gradient echo weightings.

Block 202 recites, "acquire at least one reference image." The acquisition of at least one reference image may include acquiring a low resolution MR image of a patient's complete body. For example, a patient may be imaged by the MRI system 102 using coarse settings to obtain the reference image. In some embodiments, two or more reference images may be acquired to assist in measuring magnetic field inhomogeneities.

Block 204 recites, "determine inhomogeneity distribution." To determine the inhomogeneity distribution, the at least one reference image may be analyzed to determine the spatial distribution of inhomogeneities within the image, which may be due to the subject's anatomy. The inhomogeneity distribution may be based on a magnetic field distortion map of the patient based on the at least one reference image. In some embodiments, the inhomogeneity distribution may be determined by collecting gradient echo images with different echo times, mapping the gradient echo images, and then determining the inhomogeneities based on a phase difference between the gradient echo images.

Block 206 recites, "determine correction fields." To determine the correction fields, harmonic content of the inhomogeneity distribution may be analyzed using spherical harmonic analysis. The spherical harmonic analysis may identify unwanted harmonic content in the at least one reference image (e.g. harmonic content at greater than a threshold harmonic, such as a second, third, fourth, or higher harmonic) and determine how a correction coil may be energized to generate a compensating field. The correction fields may be fields which, when applied, may cancel the unwanted harmonic content.

Block 208 recites, "store correction information." The stored correction information (e.g. a correction field map) may include the at least one reference image, the inhomogeneity distribution, and the determined correction fields. For example, the correction information may be stored in the memory 110 of FIG. 1. The correction field map may associated the correction fields with particular locations of the subject (e.g. distance along a subject, coordinate system of an imaging system, subject features, anatomy, organs).

Block 210 recites, "acquire a first image while applying respective correction fields." A first image may be acquired of at least a portion of the subject while applying correction fields suitable for that portion as reflected in the correction field map. Correction field control signals may be provided to one or more correction coils of the imaging system to generate the correction fields.

Block 212 recites, "acquire a second image while applying respective correction fields." The acquisition of the second image may be performed substantially similar to the acquisition of the first image. However, the correction fields used when acquiring the second image may be based on information in the correction field map associated with a portion of the subject being imaged in the second image.

Block 214 recites, "acquire an nth image while applying respective correction fields." The acquisition of the nth image may be performed substantially similar to the acquisition of the first image. However, the correction fields used when acquiring the nth sub-image may be based on information in the correction field map associated with a portion of the subject being imaged in the nth image. The number of images acquired may be determined by how large each image is, e.g., how large of a portion of a subject, relative to the size of the subject. Accordingly, the number of images acquired may be the number required to image the patient's entire body in some examples.

Block 216 recites, "combine the first, second, through nth images to provide a composite image." To provide a composite image of the subject, the n images may be combined, e.g., stitched together, to provide a full body high resolution MRI image of the subject in some examples. And due to basing the correction fields off a reference image of the entire patient, distortions and mismatch between the images may be reduced or eliminated so that a distortion free full body MRI image is obtained, which may aid in qualitative evaluation.

Figure 3:
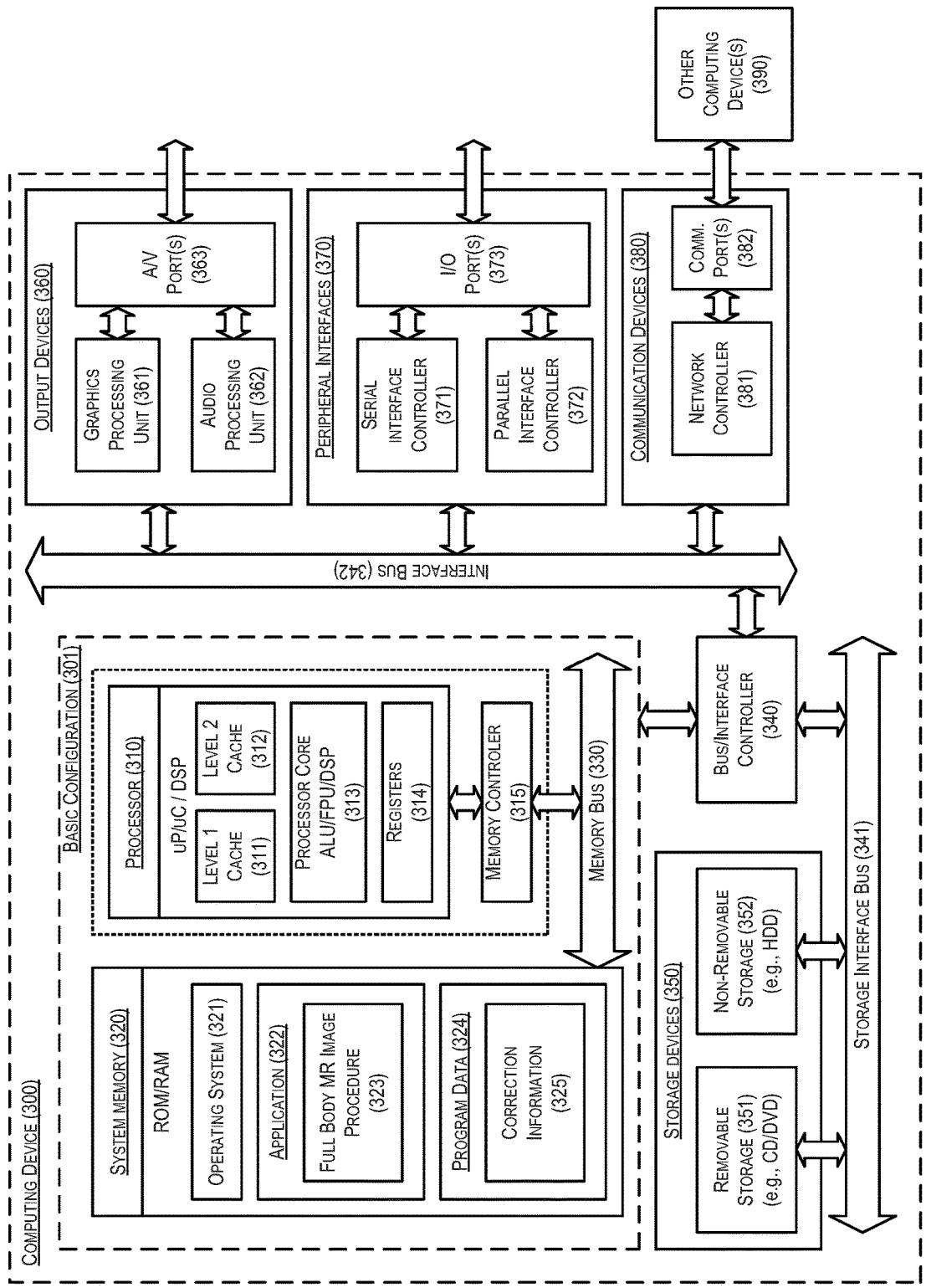
FIG. 3 is a block diagram illustrating an example computing device that is arranged for providing a distortion free full body MR image in accordance with the present disclosure.

FIG. 3 is a block diagram illustrating an example computing device 300 that is arranged for providing a distortion free full body MR image in accordance with the present disclosure. In a very basic configuration 301, computing device 300 typically includes one or more processors 310 and system memory 320. A memory bus 330 may be used for communicating between the processor 310 and the system memory 320.

Depending on the desired configuration, processor 310 may be of any type including but not limited to a microprocessor (P), a microcontroller (PC), a digital signal processor (DSP), or any combination thereof. Processor 310 may include one more levels of caching, such as a level one cache 311 and a level two cache 312, a processor core 313, and registers 314. An example processor core 313 may include an arithmetic logic unit (ALU), a floating point unit (FPU), a digital signal processing core (DSP Core), or any combination thereof. An example memory controller 315 may also be used with the processor 310, or in some implementations the memory controller 315 may be an internal part of the processor 310.

Depending on the desired configuration, the system memory 320 may be of any type including but not limited to volatile memory (such as RAM), non-volatile memory (such as ROM, flash memory, etc.) or any combination thereof. System memory 320 may include an operating system 321, one or more applications 322, and program data 324. Application 322 may include an imaging procedure 323 that is arranged to provide an MRI image as described herein. Program data 324 may include correction information, which may be one or more reference images, inhomogeneity distribution information, correction field information (e.g. correction field map), a plurality of images, and/or other information useful for the implementation of the full body MRI image procedure. In some embodiments, application 322 may be arranged to operate with program data 324 on an operating system 321 such that any of the procedures described herein may be performed. This described basic configuration is illustrated in FIG. 3 by those components within dashed line of the basic configuration 301.

Computing device 300 may have additional features or functionality, and additional interfaces to facilitate communications between the basic configuration 301 and any required devices and interfaces. For example, a bus/interface controller 340 may be used to facilitate communications between the basic configuration 301 and one or more storage devices 350 via a storage interface bus 341. The storage devices 350 may be removable storage devices 351, non-removable storage devices 352, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 320, removable storage 351 and non-removable storage 352 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 300. Any such computer storage media may be part of computing device 300.

Computing device 300 may also include an interface bus 342 for facilitating communication from various interface devices (e.g., output interfaces, peripheral interfaces, and communication interfaces) to the basic configuration 301 via the bus/interface controller 340. Example output devices 360 include a graphics processing unit 361 and an audio processing unit 362, which may be configured to communicate to various external devices such as a display or speakers via one or more A/V ports 363. Example peripheral interfaces 370 include a serial interface controller 371 or a parallel interface controller 372, which may be configured to communicate with external devices such as input devices (e.g., keyboard, mouse, pen, voice input device, touch input device, etc.) or other peripheral devices (e.g., printer, scanner, etc.) via one or more I/O ports 373. An example communication device 380 includes a network controller 381, which may be arranged to facilitate communications with one or more other computing devices 390 over a network communication link via one or more communication ports 382.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 300 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 300 may also be implemented as a personal computer including both laptop computer and non-laptop computer configurations.

Figure 4:
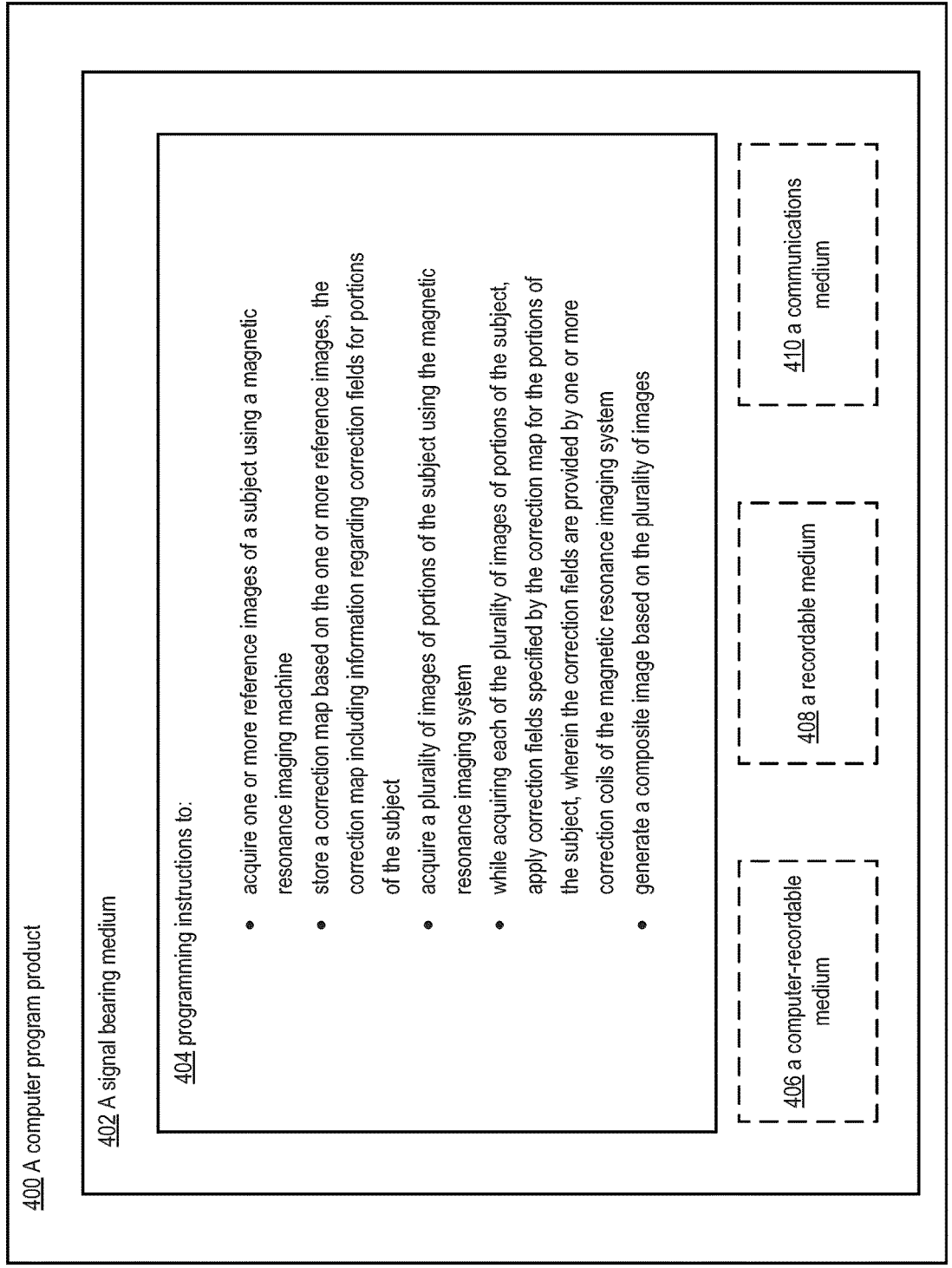
FIG. 4 is a block diagram illustrating an example computer program product that is arranged to store instructions for providing a distortion fee full body MR image in accordance with the present disclosure.

FIG. 4 is a block diagram illustrating an example computer program product 400 that is arranged to store instructions for providing a distortion fee full body MR image in accordance with the present disclosure. The signal bearing medium 402 which may be implemented as or include a computer-readable medium 406, a computer recordable medium 408, a computer communications medium 410, or combinations thereof, stores programming instructions 404 that may configure the processing unit to perform all or some of the processes previously described. These instructions may include, for example, one or more executable instructions for causing a process to acquire one or more reference images of a subject using a magnetic resonance imaging machine, store a correction field map based on the one or more reference images, the correction field map including information regarding correction fields for portions of the subject, acquire a plurality of images of portions of the subject using the magnetic resonance imaging system, while acquiring each of the plurality of images of portions of the subject, apply correction fields specified by the correction field map for the portions of the subject, wherein the correction fields are provided by one or more correction coils of the magnetic resonance imaging system, and generate a composite image based on the plurality of images.

The present disclosure is not to be limited in terms of the particular examples described in this application, which are intended as illustrations of various aspects. Many modifications and examples can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and examples are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular examples only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to examples containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 items refers to groups having 1, 2, or 3 items. Similarly, a group having 1-5 items refers to groups having 1, 2, 3, 4, or 5 items, and so forth.

While the foregoing detailed description has set forth various examples of the devices and/or processes via the use of block diagrams, flowcharts, and/or examples, such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one example, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the examples disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. For example, if a user determines that speed and accuracy are paramount, the user may opt for a mainly hardware and/or firmware vehicle; if flexibility is paramount, the user may opt for a mainly software implementation; or, yet again alternatively, the user may opt for some combination of hardware, software, and/or firmware.

In addition, those skilled in the art will appreciate that the mechanisms of the subject matter described herein are capable of being distributed as a program product in a variety of forms, and that an illustrative example of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While various aspects and examples have been disclosed herein, other aspects and examples will be apparent to those skilled in the art. The various aspects and examples disclosed herein are for purposes of illustration and are not intended to be limiting, with the true scope and spirit being indicated by the following claims.

What is claimed is:

1. A method comprising:
   acquiring, in a single process, at least one reference image of a plurality of portions of a subject using a magnetic resonance imaging system;
   determining a magnetic field inhomogeneity distribution based on the at least one reference image;
   storing a correction field map based on the magnetic field inhomogeneity distribution, the correction field map including information regarding a correction field for each of the plurality of portions of the subject;
   acquiring a plurality of images by the magnetic resonance imaging system, each of the plurality of images corresponding to a respective portion of the plurality of portions of the subject; and
   while acquiring each of the plurality of images, applying a correction field specified by the correction field map for the respective portion of the subject.

2. The method of claim 1 further comprising:
   generating a composite image based on the plurality of images.

3. The method of claim 1, wherein the correction field is configured to correct for magnetic field inhomogeneities identified from the reference image.

4. The method of claim 1 further comprising:
   determining the information regarding the correction fields for reference image based on the inhomogeneity distribution.

5. The method of claim 1, wherein acquiring a reference image using the magnetic resonance imaging system comprises:

acquiring a first reference image with a first gradient echo weight of a gradient magnetic field provided by the magnetic resonance imaging system; and acquiring a second reference image with a second gradient echo weight.

6. The method of claim 5 further comprising:

determining magnetic field inhomogeneity based on a phase difference between the first and second reference images; and generating the correction field map based on the magnetic field inhomogeneity.

7. The method of claim 1, wherein the correction field is configured to correct for certain harmonics identified by analyzing the magnetic field inhomogeneity distribution.

8. At least one non-transitory computer-readable medium encoded with executable instructions, that when executed by a computing system, causes the computing system to:

acquire, in a single process, one or more reference images of a plurality of portions of a subject using a magnetic resonance imaging machine;

determine a magnetic field inhomogeneity distribution based on the at least one reference image;

store a correction field map based on the magnetic field inhomogeneity distribution, the correction field map including information regarding correction fields for each of the plurality of portions of the subject;

acquire a plurality of images of sub-portions of the subject using the magnetic resonance imaging system, wherein each of the sub-portions corresponds to a portion of the plurality of portions of the subject;

while acquiring each of the plurality of images of portions of the subject, apply correction fields specified by the correction field map for the portions of the subject, wherein the correction fields are provided by one or more correction coils of the magnetic resonance imaging system; and generate a composite image based on the plurality of images.

9. The at least one non-transitory, computer-readable medium of claim 8 further comprising instructions, that when executed by the computing system, cause the computing system to:

determine the correction fields based on the field inhomogeneity distribution.

10. The at least one non-transitory, computer-readable medium containing of claim 9 further comprising instructions, that when executed by the computing system, cause the computing system to:

store at least the field inhomogeneity distribution, the correction fields, the one or more reference images, and the plurality of images.

11. The at least one non-transitory, computer-readable medium of claim 8, wherein the one or more reference images of the subject are acquired at a lower resolution than the plurality of images.

12. The at least one non-transitory, computer-readable medium of claim 8, wherein the instructions causing the computing system to generate a composite image based on the plurality of images further cause the computing system to stitch together the plurality of images.

13. The at least one non-transitory, computer-readable medium of claim 8, wherein the reference image comprises an image of a human body, and wherein each of the plurality of images comprise an image of a respective portion of the human body.

14. The at least one non-transitory, computer readable medium of claim 13, wherein the respective portion of the human body comprises an organ.

15. The at least one non-transitory, computer-readable medium of claim 8, wherein the correction fields are configured to correct for certain harmonics identified by analyzing the magnetic field inhomogeneity distribution.

16. A system comprising:

a magnetic resonant imaging system including a main coil and a plurality of correction coils, wherein the main coil and the correction coils provide respective magnetic fields responsive to receiving respective control signals; and a computing system coupled to the magnetic resonance imaging system, the computing system configured to provide control signals to the magnetic resonance imaging system to cause the magnetic resonance imaging system to:

acquire, in a single process, one or more reference images including a plurality of portions of a patient's body using a magnetic field provided by the main coil;

apply correction magnetic fields through at least one of the plurality of correction coils while acquiring each of a plurality of sub-images of the patient, wherein the correction field applied during the acquisition of each of the plurality of sub-images is determined based on a respective portion of the plurality of portions of the one or more reference images, and wherein the main coil provides a main magnetic field while acquiring each of the plurality of sub-images; and provide a composite image of the patient based on the plurality of sub-images.

17. The system of claim 16, wherein the magnetic resonance imaging system further comprises gradient magnetic coils configured to provide gradient magnetic fields of different gradient echo weights while acquiring the one or more reference images.

18. The system of claim 16, wherein the computing system is configured to determine a field inhomogeneity distribution based on the one or more reference images, and determine the correction magnetic fields based at least on the inhomogeneity distribution.

19. The system of claim 18, wherein the computing system further comprises a memory configured to store the one or more reference images, the inhomogeneity distribution, the correction magnetic fields, and the plurality of sub-images.

20. The system of claim 18, wherein the magnetic resonance imaging system further comprises a correction coil controller configured to control the plurality of correction coils based on the inhomogeneity distribution while acquiring each of the plurality of sub-images.

21. The system of claim 16, wherein the one or more reference images of a patient's whole body are acquired at a lower resolution than the plurality of sub-images of the patient.

22. The system of claim 16, wherein the plurality of sub-images each comprise an image of a respective portion of the patient.

23. The system of claim 16, wherein the correction field is configured to correct for certain harmonics identified by analyzing the magnetic field inhomogeneity distribution.

\* \* \* \* \*